United States Patent [19]

Drewes, Jr. et al.

[11] Patent Number: 5,300,048
[45] Date of Patent: Apr. 5, 1994

[54] FLEXIBLE, HIGHLY RADIOPAQUE PLASTIC MATERIAL CATHETER

[75] Inventors: David A. Drewes, Jr., Bloomington; Fred T. Parker, Unionville, both of Ind.

[73] Assignees: Sabin Corporation; Cook Incorporated, both of Bloomington, Ind.

[21] Appl. No.: 60,746

[22] Filed: May 12, 1993

[51] Int. Cl.$^5$ ............................................. A61M 25/00
[52] U.S. Cl. .................................. 604/280; 128/658
[58] Field of Search ......... 604/280; 128/658, DIG. 21

[56] References Cited

U.S. PATENT DOCUMENTS

| | | | |
|---|---|---|---|
| 4,027,659 | 6/1977 | Slingluff | 128/658 |
| 4,196,731 | 4/1980 | Laurin et al. | |
| 4,469,483 | 9/1984 | Becker et al. | |
| 4,636,346 | 1/1987 | Gold et al. | 604/280 |
| 4,657,024 | 4/1987 | Coneys | |
| 4,698,059 | 10/1987 | Johnson | 604/280 |
| 4,714,721 | 12/1987 | Franek et al. | |
| 4,778,455 | 10/1988 | Kousai et al. | |
| 5,009,636 | 4/1991 | Wortley et al. | 604/280 |
| 5,017,259 | 5/1991 | Kohsai | |
| 5,037,403 | 8/1991 | Garcia | 128/658 |
| 5,045,072 | 9/1991 | Castillo et al. | |
| 5,088,927 | 2/1992 | Lee | |
| 5,221,270 | 6/1993 | Parker | 604/280 |

Primary Examiner—Paul J. Hirsch
Attorney, Agent, or Firm—Richard J. Godlewski

[57] ABSTRACT

A flexible plastic material catheter having a distal tubular member portion with a greater than 75 weight percent loading of a radiopaque agent for radiographic viewing. The catheter comprises an elongated member having a proximal portion and a distal end portion with a flexible, radiopaque plastic material having a durometer lower than that of the proximal portion. The plastic material of the distal end portion comprises a homogeneous and evenly dispersed composition of a 20 weight percent base thermoplastic, elastomer material such as a polyether block amide and 80 weight percent loading of a radiopaque agent such as tungsten. This distal end portion plastic material exhibits a durometer of approximately 47 on the Shore D scale, whereas the polyether block amide material exhibits a durometer of approximately 40 on the Shore D scale. The flex modulus of the polyether block amide material is in a range of 23,000 to 75,000 pounds per square inch. The proximal end portion comprises a base thermoplastic material such as a polyamide elastomer material and a radiopaque agent of bismuth oxychloride.

20 Claims, 1 Drawing Sheet

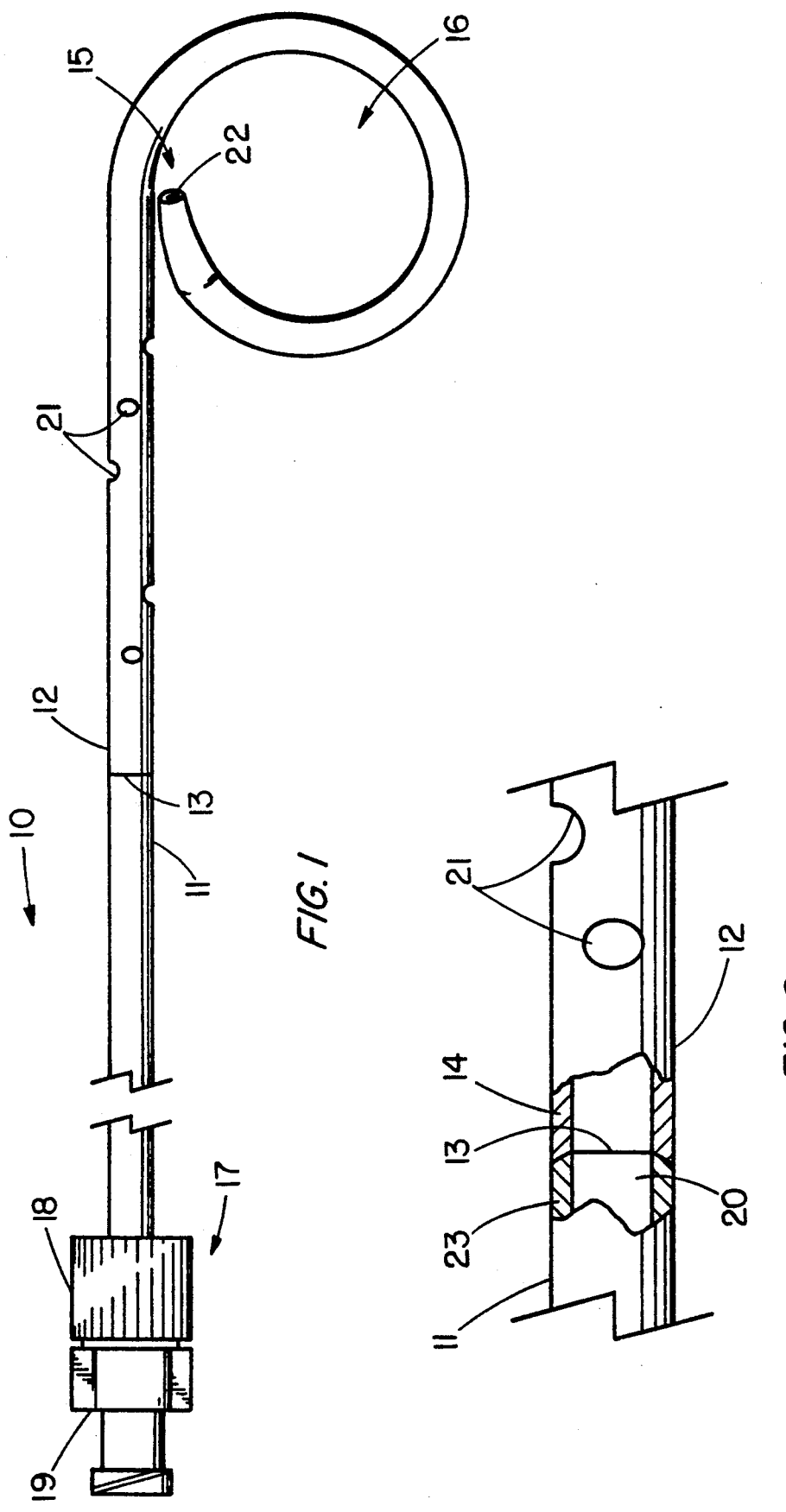

FLEXIBLE, HIGHLY RADIOPAQUE PLASTIC MATERIAL CATHETER

TECHNICAL FIELD

This invention relates generally to radiopaque catheters and, in particular, to catheters with a highly radiopaque distal portion.

BACKGROUND OF THE INVENTION

Radiopaque catheters are used to provide visualization of the catheter during a therapeutic procedure such as PTCA or kidney stone removal. Radiopaque catheters are also used in diagnostic imaging procedures for injecting contrast medium into the body of a patient. Several commercially available radiopaque catheters include increased radiopacity about the distal catheter end. Visualization of the distal catheter end is critical for locating the catheter end with respect to anatomical structures and preventing inadvertent trauma or injury of a vessel or duct during advancement of the catheter.

One approach to providing a curved, radiopaque catheter is to form the catheter body from a compound of a polyurethane material with either 20 weight percent of barium sulfate or 33.5 weight percent of bismuth subcarbonate. The distal catheter tip is formed from a compound of a polyurethane material with 49.83 weight percent of bismuth trioxide. As a result, the curved catheter body is slightly radiopaque, and the distal catheter tip is more radiopaque than the curved body.

A problem with this catheter is that the compound material forming the distal catheter tip is only moderately radiopaque in comparison to highly radiopaque materials such as solid platinum, gold, or tungsten. As a result, the radiopacity of the distal catheter tip indicates the general position thereof. However, the position of the curve in the catheter body cannot be readily discerned. Furthermore, the point at which the curved catheter body ends and the distal catheter tip begins has no readily imageable boundary. Another problem with this curved catheter is that visualization of the slightly or moderately radiopaque catheter materials is deemphasized or overcome by the images of surrounding tissues. The problem is compounded when injecting contrast medium into a blood vessel or another duct of a patient's body via the curved catheter. The contrast medium flows into the vessel or duct and surrounds the curve and the distal tip of the catheter. As a result, the curve and the distal tip of the catheter are difficult to discern or are completely obstructed by the bright image of the contrast medium.

Yet another problem with this curved catheter is that safely steering and maneuvering the catheter through tortuous vessels or ducts requires precise visualization of the distal catheter tip. When the precise position of the curve or the distal tip of the catheter is not visible, the catheter can be inadvertently advanced into anatomical structures. As a result, tissue is injured or punctured. When imaging a coronary artery or a ventricle of the heart, such trauma or injury results in serious complications and bleeding.

In view of these problems, an attempt was made to increase the radiopacity of the curved catheter by providing a plastic formulation with a higher than 75 weight percent of a radiopaque agent. This known attempt resulted in failure due to the brittleness of the plastic catheter material. Furthermore, the plastic catheter material exhibited a general loss of the desired softness and flexibility.

SUMMARY OF THE INVENTION

The foregoing problems are solved and a technical advance is achieved in an illustrative flexible, radiopaque plastic material catheter with a moderately radiopaque proximal tubular member portion and a highly radiopaque distal tubular member portion which contains greater than 75 weight percent of a radiopaque agent. As a departure in the art, the distal tubular member portion with a greater than 75 weight percent loading of a radiopaque agent is flexible and softer in durometer than the proximal portion of the catheter. The distal tubular member portion of the preferred catheter advantageously includes a homogeneous composition containing 20 weight percent of a base thermoplastic, elastomer material, preferably a polyether block amide, and an 80 weight percent radiopaque agent, preferably tungsten. The flex modulus of the base thermoplastic, elastomer material is in a range of 23,000 to 75,000 pounds per square inch. The distal tubular member portion of the catheter is lower in durometer than that of the proximal tubular member portion. The distal tubular member portion advantageously exhibits a composite durometer of approximately 47 on the Shore D scale.

The flexible plastic angiographic catheter comprises an elongated member having a passage therein. The distal portion of the elongated member comprises a first, flexible, radiopaque plastic material of a homogeneous composition containing by weight greater than 75 percent of a first radiopaque agent. The weight percent range of the radiopaque agent ranges from 76 to 95 percent. The homogeneous composition includes a base thermoplastic, elastomer material from a group consisting of a polyether block amide and a polyamide terpolymer material and a first radiopaque agent from a group consisting of tungsten, platinum, gold, silver, lead, and tantalum. The durometer of the base thermoplastic, elastic material is in a range of 25 to 72 on the Shore D scale.

The proximal portion of the elongated member comprises a flexible, radiopaque material of a base thermoplastic material from a group consisting of a polyester elastomer, a polyurethane, a polyamide elastomer, and a polyether block amide and a radiopaque agent from a group consisting of bismuth oxychloride, bismuth subcarbonate, bismuth trioxide, barium sulfate, and tungsten.

As a result, this flexible plastic material catheter advantageously includes a highly radiopaque distal tubular member portion which is highly visible radiographically while still maintaining a high degree of flexibility and softness for introduction to the angiographic site. Even with an extremely high loading of a radiopaque agent, the distal tubular portion retains its material integrity while still remaining soft and flexible. The use of a high density radiopaque agent, such as tungsten in combination with a base thermoplastic, elastomer material, also advantageously contributes to the material integrity of the soft and flexible distal tubular member portion.

BRIEF DESCRIPTION OF THE DRAWING

FIG. 1 depicts a longitudinal view of an illustrative angiographic catheter of the present invention with a preformed pigtail configuration in the highly radiopaque, distal portion; and FIG. 2 depicts a partially sectioned, longitudinal view of the catheter of FIG. 1 at the bond between the moderately radiopaque proximal portion and the highly radiopaque distal portion.

DETAILED DESCRIPTION

FIG. 1 depicts a longitudinal view of an illustrative flexible plastic, angiographic catheter 10 which is an elongated member with moderately radiopaque proximal tubular member portion 11 and highly radiopaque, distal tubular member portion 12 fixedly attached thereto at thermal bond 13. Highly radiopaque distal tubular member portion 12 is formed from a flexible, highly radiopaque plastic material 14 comprising, for example, a homogeneous and uniformly dispersed composition of a base thermoplastic elastomer material and a radiopacifying agent. Flexible, highly radiopaque plastic material 14, as depicted in FIG. 2, is preferably formed of approximately 20 weight percent of a base thermoplastic, elastomer material and 80 weight percent of a radiopacifying agent. When catheter 10 is introduced into the vascular system of a patient through a commercially available access sheath, the catheter is advanced over a wire guide through the vessels of a patient until the highly radiopaque, distal portion is positioned at a desired angiography site. Catheter 10 includes distal end 15 with preformed loop or pigtail configuration 16 positioned proximately for atraumatic positioning of the catheter past anatomical structures such as the tricuspid valve of the heart.

Catheter 10 further includes proximal end 17 with connector cap 18 and female Luer lock connector 19 positioned thereabout for grasping by the physician and manipulation of the catheter. Catheter 10 also further includes passage 20 extending longitudinally therein between proximal end 17 and distal end 15. When the highly radiopaque, distal portion is positioned at the desired angiography site, a well-known syringe (not shown) filled with contrast medium is connected to Luer lock connector 19. The contrast medium is injected to the angiography site via passage 20. The contrast medium exits passage 20 at sideports 21 and end port 22, which are formed in the highly radiopaque, distal portion of the catheter.

FIG. 2 depicts a partially sectioned, longitudinal view of the catheter of FIG. 1 at thermal bond 13 where moderately radiopaque proximal portion is fixedly attached to highly radiopaque distal portion 12 formed from flexible, highly radiopaque plastic material 14. The highly radiopaque distal portion extends for a sufficient length of the catheter to include a loop or pigtail configuration 16 and sideports 21 for brightly imaging and positively visualizing the position of the catheter during advancement to the desired site and the subsequent injection of contrast medium.

Proximal tubular member portion 11 of catheter 10 is, for example, an approximately 100 cm length of flexible, moderately radiopaque, plastic material 23 with a 0.067" outside diameter (5 French) and a 0.050" inside diameter, which exhibits sufficient pushability for advancing the catheter to a desired site. The flexible, moderately radiopaque, plastic material 23 comprises a base thermoplastic, elastomer material and a radiopaque agent in a weight percent range of 15 to 40. The base thermoplastic, elastomer material preferably comprises a polyamide elastomer such as a commercially available elastomeric nylon 12 material. Alternative base thermoplastic, elastomer materials are from a group consisting of polyester elastomers, polyurethanes, and a polyether block amide. The radiopaque agent preferably comprises 25 weight percent of bismuth oxychloride, which is easily dispersable through the base thermoplastic, elastomer material and exhibits very good surface characteristics. Bismuth oxychloride is also white in color, which allows the catheter to assume a number of different colors with the addition of a coloring pigment. Alternative radiopaque agents are from a group consisting of bismuth subcarbonate, bismuth trioxide, barium sulfate, and tungsten.

Distal tubular member portion 12 of catheter 10 is, for example, an approximately 8-9 cm length of flexible, highly radiopaque, plastic material 14 with a 0.066" outside diameter (5 French) and a 0.045" inside diameter, which is softer and more flexible and has a respective durometer lower than that of the proximal tubular member portion. Flexible, highly radiopaque, plastic material 14 comprises a homogeneous and uniformly dispersed composition of a base thermoplastic, elastomer material and a high density radiopaque agent in a weight percent range of 75 to 95. The high density radiopaque agent has a density in excess of 10 grams per cubic centimeter and is from a group consisting of tungsten, platinum, gold, silver, lead, and tantalum. Tungsten with a density of 19.29 grams per cubic centimeter is preferred due to its availability and relative low cost.

The homogeneous and uniformly dispersed composition of plastic material 14 includes approximately 20 weight percent of a base thermoplastic, elastomer material such as a polyether block amide with a durometer of 40 on the Shore D scale, which is commercially available from Elf Atochem North America of Birdsboro, Pa., or a polyamide terpolymer with a durometer of 40 on the Shore D scale, which is commercially available from Huls America of Piscataway, N.J. The base thermoplastic, elastomer material can have a durometer in a range of 25 to 72 on the Shore D scale. With 80 weight percent tungsten, the composite durometer of preferred distal tubular member portion 12 is approximately 47 on the Shore D scale. The flexibility of the preferred base thermoplastic elastomer material exhibits a flex modulus in a range of 23,000 to 75,000 pounds per square inch.

As previously suggested, the homogeneous and uniformly dispersed composition of plastic material 14 further includes approximately 80 weight percent of a radiopacifying agent such as high purity, micronized tungsten powder (40 micron), which is commercially available from Atlantic Equipment Engineers of Bergenfield, N.J. Tungsten is compounded with a base thermoplastic, elastomer material at a weight percent in a range from 76 to 95. The required volume of tungsten is small enough to allow the desirable physical characteristics of the base material to be exhibited. The distal portion of the catheter exhibits softness and flexibility for atraumatic insertion to the desired angiographic site.

Catheter 10 is preferably shipped and stored without exposure to high temperatures in a hermetically sealed package that is nonpermeable to light for preventing degradation of flexible, highly radiopaque plastic material 14.

Flexible, highly radiopaque plastic material 14 is formed by, for example, drying the base thermoplastic elastomer material to a moisture content below 0.025 percent. The dried, pelleted base material is loaded into a pellet feeder, and the tungsten powder is loaded into a powder feeder of a feeder system attached to a commercially available, corotating twin screw machine from, for example, Werner Pfleiderer Corporation of Ramsey, N.J., or American Leistritz Corporation of Somerville, N.J. The feeder system preferably has an accuracy of 2 percent by weight or better and is commercially available from, for example, K-Tron Corporation of Pitman, N.J., or Thayer Scale of Pembroke, Mass. The twin screw machine is heat soaked for a time period such as 15 minutes. The pellet feeder is started first, and the melt quality of the material is visually verified to be certain that the material is clean, clear, smooth, and free of any internal bubbles. Then the powder feeder is started, and the melt quality of the compounded material is visually verified to be certain that the material is solid black and has no lumps apparent without magnification. After the melt quality appears to be acceptable, the machine is allowed to run for about 5 to 10 minutes before starting the extrudate through a water cooling trough such as is commercially available from Werner Pfleiderer or American Leistritz, as listed above, and a strand pelletizer such as is commercially available from ConAir Jetro of Bay City, Mich., or American Leistritz, as listed above. Finally, the compounded material is processed through a conventional, commercially available, single screw extruder with the appropriate tooling and ancillary equipment for yielding an approximately 8-9 cm length of highly radiopaque distal tubular member portion 12, which has a 0.066" outside diameter (5 French) and a 0.045" inside diameter.

Pigtail 16 is, for example, 1.3 cm in diameter. Alternative atraumatic distal end configurations such as open loops and pigtails oriented transversely with respect to the axis of the catheter are contemplated. Sideports 21 are, for example, 0.032" in diameter. Bond 13 is positioned in a range between 4.5 and 5.5 cm proximal the distal-most point on the preformed pigtail surface when measuring along the axis of catheter 10. Bond 13 is formed by heat, but other methods of bonding such as the use of adhesive or mechanical means are contemplated.

It is to be understood that the above-described angiography catheter with a highly radiopaque distal portion is merely an illustrative embodiment of the principles of this invention and that other radiopaque catheters may be devised by those skilled in the art without departing from the spirit and scope of this invention. For example, guiding catheters, angioplasty balloon catheters, drainage catheters, and any other medical catheter that desirably includes a highly radiopaque portion are contemplated. It is further contemplated that the catheter include one or more preformed curves and bends along the axis thereof for facilitating introduction into various blood vessels or ducts with well-known anatomical curvatures. It is also further contemplated that the highly radiopaque material include a stabilizer package having one or more antioxidin chemicals, which result in heat stabilization, and one or more ultraviolet stabilizing chemicals, which protect the material from light degradation, in order to extend the shelf life of the catheter.

What is claimed is:

1. A flexible plastic catheter comprising:
an elongated member having a passage therein and including a proximal portion of a second, flexible, radiopaque plastic material and a distal end portion of a first, flexible, radiopaque plastic material having a durometer lower than said second, flexible, radiopaque plastic material, said first, flexible, radiopaque plastic material of said distal end portion comprising a homogeneous composition containing by weight greater than 75 percent of a radiopaque agent.

2. The catheter of claim 1 wherein said first, flexible, radiopaque plastic material of said distal end portion has a higher weight percent of a radiopaque agent than said second, flexible, radiopaque plastic material of said proximal portion.

3. The catheter of claim 1 wherein said homogeneous composition of said distal end portion comprises a range of approximately 76 to 95 weight percent of said radiopaque agent.

4. The catheter of claim 1 wherein said radiopaque agent has a density greater than 10 grams per cubic centimeter.

5. The catheter of claim 1 wherein said radiopaque agent is from a group consisting of tungsten, platinum, gold, silver, lead, and tantalum.

6. The catheter of claim 1 wherein said second, flexible, radiopaque plastic material comprises a thermoplastic material from a group consisting of a polyester elastomer, a polyurethane, a polyamide elastomer, and a polyether block amide.

7. The catheter of claim 1 wherein said second, flexible, radiopaque plastic material comprises a nylon elastomer.

8. The catheter of claim 1 wherein said second, flexible, radiopaque plastic material comprises an other radiopaque agent from a group consisting of bismuth oxychloride, bismuth subcarbonate, bismuth trioxide, barium sulfate, and tungsten.

9. The catheter of claim 1 wherein said homogeneous composition includes a base thermoplastic, elastomer material.

10. The catheter of claim 9 wherein said base thermoplastic, elastomer material has a durometer in a range of 25 to 72 on the Shore D scale.

11. The catheter of claim 10 wherein said base thermoplastic, elastomer material is from a group consisting of a polyether block amide and a polyamide terpolymer material.

12. The catheter of claim 11 wherein said base thermoplastic, elastomer material has a flex modulus in a range of 23,000 to 75,000 pounds per square inch.

13. The catheter of claim 1 wherein said first, flexible, radiopaque plastic material has a composite durometer of approximately 47 on the Shore D scale.

14. A flexible plastic catheter comprising:
a proximal tubular member of a second, flexible, radiopaque material including a base thermoplastic material from a group consisting of a polyester elastomer, a polyurethane, a polyamide elastomer, and a polyether block amide, and a second radiopaque agent from a group consisting of bismuth oxychloride, bismuth subcarbonate, bismuth trioxide, barium sulfate, and tungsten; and
a distal tubular member attached to said proximal tubular member and having a durometer lower than said proximal tubular member, said distal tubular member comprising a first, flexible, radiopaque material of a homogeneous composition containing a base thermoplastic, elastomer material and greater than 75 weight percent of a first radiopaque agent.

15. The catheter of claim 14 wherein said base thermoplastic, elastomer material has a durometer in a range of 25 to 72 on the Shore D scale.

16. The catheter of claim 15 wherein said base thermoplastic, elastomer material is from a group consisting of a polyether block amide and a polyamide terpolymer material.

17. The catheter of claim 16 wherein said base thermoplastic, elastomer material has a flex modulus in a range of 23,000 to 75,000 pounds per square inch.

18. The catheter of claim 14 wherein said distal tubular member includes a preformed pigtail configuration proximate a distal end thereof.

19. The catheter of claim 14 wherein said distal tubular member includes a sideport communicating with a passage extending longitudinally therein.

20. A flexible plastic catheter comprising:

a proximal tubular member of a second, flexible, radiopaque material including a base thermoplastic, elastomer material of a polyamide elastomer and a second radiopaque agent of approximately 25 weight percent of bismuth oxychloride; and a distal tubular member attached to said proximal tubular member and having a pigtail configuration proximate a distal end thereof, said distal member comprising a first, flexible, radiopaque material of a homogeneous composition having a composite durometer of approximately 47 on the Shore D scale and lower than the durometer of said proximal tubular member and containing a base thermoplastic, elastomer material of polyether block amide having a flex modulus in a range from 23,000 to 75,000 pounds per square inch, said homogeneous composition also containing approximately 80 weight percent of tungsten.

* * * * *